United States Patent [19]

Kyker et al.

[11] 4,233,251

[45] Nov. 11, 1980

[54] PROCESS FOR PREPARING HEXACHLOROCYCLOPENTADIENE

[75] Inventors: Glendon D. Kyker, Glen Ellyn; Kalidas Paul, Bolingbrook, both of Ill.

[73] Assignee: Velsicol Chemical Corporation, Chicago, Ill.

[21] Appl. No.: 49,854

[22] Filed: Jun. 18, 1979

[51] Int. Cl.$^3$ .............................................. C07C 23/08
[52] U.S. Cl. ...................................... 570/220; 570/186
[58] Field of Search ...................................... 260/648 C

[56] References Cited

U.S. PATENT DOCUMENTS

| 3,073,869 | 1/1963 | Hanna et al. | 260/648 C |
|---|---|---|---|
| 3,763,250 | 10/1973 | Rai et al. | 260/648 C |
| 3,988,369 | 10/1976 | Pearson | 260/648 C |

*Primary Examiner*—Curtis R. Davis
*Attorney, Agent, or Firm*—Dietmar Olesch; Robert J. Schwarz

[57] ABSTRACT

There is disclosed a process for the production of hexachlorocyclopentadiene comprising the steps of:

(a) reacting liquid cyclopentadiene and chlorine at a temperature of from about 0 to about 100 degrees centigrade until a minimum of four chlorine atoms has been added per mole of cyclopentadiene to form a first-stage product;

(b) heating the resultant liquid reaction product of step (a) in a second stage at a temperature of from about 140 degrees centigrade to below about 200 degrees centigrade with chlorine in the presence of from about 0.0001 percent to about 5.0 percent (by weight) of a phosphorus compound until the reaction products of step (a) contain an average of about six chlorine atoms per molecule, based on cyclopentadiene starting material, wherein said phosphorus compound is

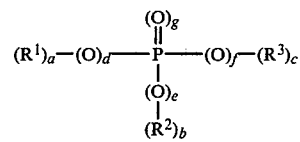

wherein a, b, c, d, e, f, and g are integers independently selected from the group consisting of 0 and 1, and $R^1$, $R^2$, and $R^3$, are independently selected from the group consisting of hydrogen, hydroxyl, flourine, chlorine, bromine, iodine, alkyl containing from about 1 to 12 carbon atoms, phenyl, and halophenyl;

(c) vaporizing and heating the resulting reaction products of step (b) in a third stage in the presence of chlorine to a temperature of about 450 degrees centigrade until at least a major portion of said products are converted to hexachlorocyclopentadiene; and (d) recovering therefrom hexachlorocyclopentadiene.

10 Claims, No Drawings

PROCESS FOR PREPARING HEXACHLOROCYCLOPENTADIENE

FIELD OF THE INVENTION

An improved process for preparing hexachlorocyclopentadiene wherein a partially chlorinated cyclopentadiene is reacted with chlorine in the presence of a phosphorus compound.

DESCRIPTION OF THE PRIOR ART

A process for the production of high purity hexachlorocyclopentadiene by the direct, non-catalytic reaction of liquid cyclopentadiene and chlorine is disclosed in U.S. Pat. No. 3,073,869. This process may be used to produce hexachlorocyclopentadiene in commercially practicable yields without the necessity of extensive purification procedures. In this process, liquid cyclopentadiene and chlorine are reacted in a first stage at a temperature of from about 0 to about 100 degrees centigrade until at least four chlorine atoms per mole of cyclopentadiene have been added, the resulting liquid reaction mixture is heated in a second stage at a temperature of from about 140 degrees centigrade to below 200 degrees centigrade with chlorine until the cyclopentadiene reactant contains an average of about six chlorine atoms per mole of cyclopentadiene, and the reaction mixture is vaporized and heated in a third stage in the presence of chlorine to a temperature of above 450 degrees centigrade.

The third stage of the process of U.S. Pat. No. 3,073,869 to conducted in the vapor phase. In this stage solid products often form which plug up the vapor phase reactor; this coking eventually forces one to shut down the reaction until the vapor phase reactor can be unplugged.

Shutting down the process of U.S. Pat. No. 3,073,869 is to be avoided as much as possible, for it usually takes an inordinately long period of time to start it up again. Thus, for example, when this process is conducted on a commercial scale, it usually takes from about 8 to about 48 hours to start up the dead first stage reaction in the second-stage reactor.

It is an object of this invention to provide an improved process wherein coking in the vapor phase stage is minimized. It is a further object of this invention to provide an improved process wherein the time it takes to start up a dead reaction in the second-stage reactor is substantially reduced.

DETAILED DESCRIPTION OF THE INVENTION

In accordance with this invention, there is provided a process for the production of hexachlorocyclopentadiene comprising the steps of:

(a) reacting liquid cyclopentadiene and chlorine at a temperature of from about 0 to about 100 degrees centigrade until a minimum of four chlorine atoms has been added per mole of cyclopentadiene;

(b) heating the resultant liquid reaction product of step (a) in a second stage at a temperature of from about 140 degrees centigrade to below about 200 degrees centigrade with chlorine in the presence of from about 0.0001 percent to about 5.0 percent (by weight) of a phosphorus compound until the reaction products of step (a) contain an average of about six chlorine atoms per molecule, based on cyclopentadiene starting material, wherein said phosphorus compound is

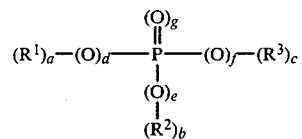

wherein a, b, c, d, e, f, and g are integers independently selected from the group consisting of 0 and 1, and $R^1$, $R^2$, and $R^3$ are independently selected from the group consisting of hydrogen, hydroxyl, fluorine, chlorine, bromine, iodine, alkyl containing from about 1 to about 12 carbon atoms, phenyl, and halophenyl;

(c) vaporizing and heating the resulting reaction products of step (b) in a third stage in the presence of chlorine to a temperature of above 450 degrees centigrade until at least a major portion of said products are converted to hexachlorocyclopentadiene; and (d) recovering therefrom hexachlorocyclopentadiene.

Applicants have discovered that, unexpectedly, the novel process of this invention allows them to obtain a product with higher proportions of the desired hexachloro- and heptachloro- derivatives, increases the rate of hexachlorocyclopentadiene production in the vapor phase step, reduces coking and the line blockage caused by it, and reduces the amount of start up time required for a dead reaction in the second-stage reactor.

The first stage of the present process involves reacting liquid cyclopentadiene and chlorine at relatively low temperatures so as to add a minimum of four chlorine atoms per mole of cyclopentadiene. Generally the temperature for this liquid phase reaction should be maintained between about 0° C. and about 100° C., it being preferred to perform this reaction at a temperature below about 60° C., with optimum practical results being obtained at reaction temperatures between about 20°–60° C.

During the first stage chlorination reaction, it is necessary that the reaction mixture be saturated with chlorine so as to substantially prevent the formation of polymer. Likewise, due to the tendency of cyclopentadiene to polymerize in the presence of chlorine, it is necessary to prevent build-up of cyclopentadiene. This undesired polymerization can be eliminated by quick dilution of the cyclopentadiene.

While the theoretically required amount of chlorine is 2 moles per mole of cyclopentadiene, the necessity of maintaining a saturated reaction mixture so as to prevent polymerization requires the use of excess chlorine. The necessary excess varies with the reaction temperature, but generally cyclopentadiene:chlorine ratios between about 1:2 and 1:4 are sufficient, the exact concentration not being critical. Actually a chlorine excess of above 50% is not of consequential value.

Superatmospheric pressure is not required for this low temperature reaction, but since there is involved a gaseous reactant, a closed reaction vessel is employed for the first stage. The reaction time is relatively short, up to about 5 hours, and is dependent on the reaction temperature, pressure (if employed), concentration of reactants, type of equipment, and whether the process is conducted as a batch or continuous operation.

The resulting reaction mixture from the first stage low temperature chlorination reaction contains a mixture of compounds of the formula

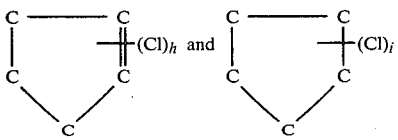

wherein h is from 1 to about 8 and i is about 4 to about 8; said reaction mixture contains from about 68 to about 72 percent (by weight) of chlorine. It is preferred that h be selected from the group consisting of 3, 4, 5, and 6 and that said reaction mixture contain about 70 percent (by weight) of chlorine.

The resulting reaction mixture from the first stage low temperature chlorination reaction is then further chlorinated in the liquid phase with chlorine in a second stage closed reaction vessel in the presence of a phosphorus compound.

In this second stage reaction of the present process, the reaction temperature is of critical importance. The second stage reaction, in essence, is the reaction of the previously described first stage reaction product and chlorine at a temperature between about 140° C. and below 200° C., and preferably between about 150° C. and about 185° C., to produce a reaction product containing an average of 6 chlorine atoms per molecule of cyclopentadiene starting material. As in the case of the first stage chlorination, no catalyst need not be employed. At temperatures above this critical area, as discussed previously, there is produced octachlorocyclopentene.

As in the first stage reaction, this second stage reaction is performed using atmospheric pressure, although superatmospheric pressures can be advantageous.

Theoretically, 2 moles of chlorine are required per mole of tetrachlorocyclopentane material. Tetrachlorocyclopentane:chlorine ratios between about 1:2 and 1:6 are satisfactory. The presence of chlorine in amounts above this 200% excess is not of value.

While each of the various liquid phase chlorination reactions of the present process can be performed as a batch process, it is a preferred embodiment of the present process to use it as a continuous process. This is particularly so for the first two stages since they are both liquid phase chlorination reactions, the second using the product of the first as its starting material. In utilizing a continuous process for the first two reactions, the chlorine can be introduced countercurrent to the process stream, i.e., being introduced into the second stage reaction and then into the first stage reaction.

In the process of this invention, the liquid reaction mass from stage one of the process is heated at a temperature of from about 140° to below about 200° degrees centigrade with chlorine in the presence of from about 0.0001 percent to about 5.0 percent (by weight) of a preferred phosphorus compound until the cyclopentadiene contains an average of about six chlorine atoms per mole of cyclopentadiene. It is preferred to use from about 0.0003 to about 1.0 percent (by weight of the liquid reaction mass from stage one) of said compound in this second stage, although it is more preferred to use from about 0.0005 to about 0.009 percent (by weight) of said phosphorous compound; it is most preferred to use from about 0.0006 to about 0.0008 percent (by weight) of said phosphorous compound in the second stage of this process.

The preferred phosphorus compound used in the second stage of the process of this invention is

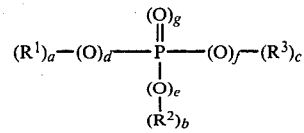

wherein a, b, c, d, e, f, and g are integers independently selected from the group consisting of 0 and 1 and $R^1$, $R^2$, and $R^3$ are independently selected from the group consisting of hydrogen, hydroxyl, fluorine, chlorine, bromine, iodine, alkyl containing from about 1 to about 12 carbon atoms, phenyl, and halophenyl.

By way of illustration and not limitation, some of the phosphorus compounds which may be used in applicant's process include, for example, such phosphines as $EtPH_2$; $PrPH_2$; iso-$BuPH_2$; iso-$AmPH_2$; n-$C_7H_{15}PH_2$; n-$C_8H_{17}PH_2$; $PhPH_2$; 4-$ClC_6H_4PH_2$; 4-$BrC_6H_4PH_2$; $Et_2PH$; Me(iso-Pr)PH; (isoPr)$_2$PH; EtBuPH; $Bu_2PH$; iso-Pr(isoBu)PH; (iso-Bu)$_2$PH; (iso-$Am_2$PH; $Ph_2PH$; (2-$ClC_6H_4$)$_2$PH; (1-$C_{10}H_7$)$_2$PH; ($ClCH_2$)$_3$P; $Et_3P$; (iso-Pr)$_3$P; $Bu_3P$; (iso-Bu)$_3$P; $Am_3P$; (MeEtCh)$_3$P; (iso-Am)$_3$P; ($C_6H_{12}$)$_3$P; ($C_7H_{15}$)$_3$P; ($C_8H_{17}$)$_3$P; $Ph_3P$; (2-$ClC_6H_4$)$_3$P; (3-$ClC_6H_4$)$_3$P; (4-$ClC_6H_4$)$_3$P; (1-$C_{10}H_7$)$_3$P; $Me_2EtP$; $Me_2$(4-$BrC_6H_4$)P; $Et_2MeP$; $Et_2PrP$; $Et_2$(iso-Am)P; $Et_2PhP$; $Et_2$(4-$ClC_6H_4$)P; $Et_2$(4-$BrC_6H_4$)P; $Et_2$(1-$C_{10}H_7$)P; $Pr_2PhP$; (4-$BrC_6H_4$)$_3$P; $Bu_2PhP$; iso-$Bu_2PhP$; (iso-Am)$_2$PhP; ($C_6H_{13}$)$_2$PhP; ($C_7H_{15}$)$_2$PhP; ($C_8H_{17}$)$_2$PhP; $Ph_2MeP$; $Ph_2EtP$; $Ph_2$(4-$ClC_6H_4$)P; $Ph_2$(4-$BrC_6H_4$)P; ($CH_2CH_2$)$_2$PPh; $CH_2(CH_2CH_2$)$_2$PPh; Et(iso-Pr)(iso-Bu)P; EtPh(4-$BrC_6H_4$)P; Ph(4-$BrC_6H_4$)(3-$C_5H_4N$)P; and the like.

Halophosphines may also be used in the process of this invention. Thus, for example, one may use such halophosphines as $EtPCl_2$; $PrPCl_2$; iso-$PrPCl_2$; $BuPCl_2$; $BuPBr_2$; iso-$BuPCl_2$; iso-$AmPCl_2$; Me($CH_2$)$_5$CHCl $CH_2PCl_2$; $PhPCl_2$; $PhPBr_2$; 4-$ClC_6H_4PCl_2$; 4-$BrC_6H_4PCl_2$; 1-$C_{10}H_7PCl_2$; 1-$C_{10}H_7PBr_2$; 2-$C_{10}H_7PCl_2$; $MeEtPCl$; $MeEtPBr$; $Et_2PBr$; $Pr_2PCl$; $Pr_2PBr$; $Bu_2PCl$; $Bu_2PBr$; $MePhPCl$; $MePhPBr$; $EtPhPCl$; $EtPhPBr$; $Ph_2PCl$; $Ph_2PBr$; (4-$BrC_6H_4$)PhPCl; (2-$ClC_6H_4$)$_2$PCl; (2-$ClC_6H_4$)$_2$PBr; (4-$ClC_6H_4$)$_2$PCl; (4-$ClC_6H_4$)$_2$PBr; (1-$C_{10}H_7$)$_2$PCl; (1-$C_{10}H_7$)$_2$PBr; and the like.

Tertiary phosphine oxides, also may be used in the process of this invention. Thus, for example, one may use compounds such as $Me_3PO$; ($ClCH_2$)$_3$PO; $Et_3PO$; $Pr_3PO$; $Bu_3PO$; ($CH_2$:CMe $CH_2$)$_3$PO; $Am_3PO$; (iso-Am)$_3$PO; (n-$C_6H_{13}$)$_3$PO; (n-$C_7H_{15}$)$_3$PO; $Ph_3PO$; (3-$O_2NC_6H_4$)$_3$PO; (3-$H_2NC_6H_4$)$_3$PO; (3-$Me_2NC_6H_4$)$_3$PO; (4-$Me_2NC_6H_4$)$_3$PO; (4-$Et_2NC_6H_4$)$_3$PO; (2-$ClC_6H_4$)$_3$PO; (3-$ClC_6H_4$)$_3$PO; (4-$ClC_6H_4$)$_3$PO; (3-$MeOC_6H_4$)$_3$PO; (2-$MeC_6H_4$)$_3$PO; (3-$MeC_6H_4$)$_3$PO; (4-$MeC_6H_4$)$_3$PO; (4-Me-3-$O_2NC_6H_3$)$_3$PO; (4-$HO_2C$ $C_6H_4$)$_3$PO; ($PhCH_2$)$_3$PO; (4-$O_2NC_6H_4CH_2$)$_3$PO; (2,4-$Me_2C_6H_3$)$_3$PO; (2,5-$Me_2C_6H_3$)$_3$PO; (2,4,5-$Me_3C_6H_2$)$_3$PO; (1-$C_{10}H_7$)$_3$PO; (2-$PhC_6H_4$)$_3$PO; (4-$PhC_6H_4$)$_3$PO; tri-2-pyrrylphosphine oxide; tri-2-pyridylphosphine oxide; tri-3-indolylphosphine oxide; tri-(2-methyl-3-indolyl) phosphine oxide; $Me_2EtPO$; $Me_2PhPO$; $Me_2$(4-$Me_2NC_6H_4$)PO; $Me_2$(4$MeC_6H_4$)PO; $Me_2$(4-$HO_2C$ $C_6H_4$)PO; $Me_2$(2,5-$Me_2C_6H_3$)PO; $Me_2$($PhCH_2$)PO; $Et_2MePO$; $Et_2PrPO$; $Et_2PhPO$; $Et_2$(4-$Me_2NC_6H_4$)PO;

Et$_2$(4-MeC$_6$H$_4$)PO; Et$_2$(4-HO$_2$C C$_6$H$_4$)PO; (BrCH$_2$ CMeBr Ch$_2$)$_2$PhPO; (BrCH$_2$CMeBr CH$_2$)$_2$(4-BrC$_6$H$_4$)PO; (n-C$_6$H$_{13}$)$_2$PhPO; (n-C$_8$H$_{17}$)$_2$PhPO; Ph$_2$MePO; Ph$_2$(Cl$_3$C)PO; Ph$_2$EtPO; Ph$_2$(Me CO)PO; Ph$_2$(EtO$_2$C CH$_2$)PO; Ph$_2$(CH$_2$:CH CH$_2$)PO; Ph$_2$(Me CO CH$_2$)PO; Ph$_2$(Me Co CH$_2$)PO; Ph$_2$(iso-Pr)PO; Ph$_2$(iso-Bu)PO; Ph$_2$(iso-Am)PO; Ph$_2$(4-Me$_2$NC$_6$H$_4$)PO; Ph$_2$(PhCH$_2$)PO; Ph$_2$(3-HO$_2$C C$_6$H$_4$)PO; Ph$_2$(4-MeC$_6$H$_4$)PO; Ph$_2$(Ph CHOH)PO; Ph$_2$(Ph$_3$C)PO; Ph$_2$(Ph CO CH$_2$ CHPh)PO; Ph$_2$(4-ClC$_6$H$_4$ CO CH$_2$ CHPh)PO; (PhCH$_2$)$_2$PhPO; (4-MeC$_6$H$_4$)$_2$MePO; (4-MeC$_6$H$_4$)$_2$(4-ClC$_6$H$_4$)PO; (4-PhC$_6$H$_4$)$_2$MePO; (4-PhC$_6$H$_4$)$_2$(CH$_2$:CH CH$_2$)PO; MeEtPhPO; MePrPhPO; EtPrPhPO; MePh(4-Me$_2$NC$_6$H$_4$)PO; MePh(PhCH$_2$)PO; EtPh(PhCH$_2$)PO; BuPh(4-Ph CO OC$_6$H$_4$)PO; and the like.

One may also use phosphonic acids in the process of this invention such as, e.g., MePO(OH)$_2$ EtPO(OH)$_2$; CH$_2$:CHPO(OH)$_2$; PrPO(OH)$_2$; CH$_2$:CH CH$_2$PO(OH)$_2$; iso-PrPO(OH)$_2$; CH$_2$:CMe PO(OH)$_2$; BuPO(OH)$_2$; CH$_2$:CH CH:CHPO(OEt)$_2$; iso-BuPO(OH)$_2$; Me$_2$C:CH PO(OH)$_2$; AmPO(OH)$_2$; Dibutyl isoprenephosphonate; iso-AmPO(OH)$_2$; n-C$_6$H$_{13}$PO(OH)$_2$; n-C$_7$H$_{15}$PO(OH)$_2$; n-C$_8$H$_{17}$PO(OH)$_2$; Me$_3$C CH$_2$ CMe:CHPO(OH)$_2$; n-C$_9$H$_{19}$PO(OH)$_2$; n-C$_{10}$H$_{21}$PO(OH)$_2$; n-C$_{12}$H$_{25}$PO(OH)$_2$; n-C$_{14}$H$_{29}$PO(OH)$_2$; n-C$_{16}$H$_{33}$PO(OH)$_2$; n-C$_{16}$H$_{33}$CH:C(PO$_3$H$_2$)C$_{17}$H$_{35-n}$; PhCH$_2$PO(OH)$_2$; 4-O$_2$NC$_6$H$_4$CH$_2$PO(OH)$_2$; 4-H$_2$NC$_6$H$_4$CH$_2$PO(OH)$_2$; 2-HO-5-O$_2$NC$_6$H$_3$CH$_2$PO(OH)$_2$; 2-MeO-5-OHC C$_6$H$_3$CH$_2$PO(OH)$_2$; 4-MeC$_6$H$_4$CH$_2$PO(OH)$_2$; 4-EtC$_6$H$_4$CH$_2$PO(OH)$_2$; 2,4-Me$_2$C$_6$H$_3$CH$_2$PO(OH)$_2$; 2-Me-5-iso-Pr C$_6$H$_3$CH$_2$PO(OH)$_2$; 4-BuC$_6$H$_4$CH$_2$PO(OH)$_2$; 1-C$_{10}$H$_7$CH$_2$PO(OH)$_2$; (3,4-Tetramethylenephenyl)methane phosphonic acid; 4-PhC$_6$H$_4$CH$_2$PO(OH)$_2$; 9-Penanthrylmethanephosphonic acid; (PhCH$_2$)$_2$CHPO(OH)$_2$; 2-Indenephosphonic acid; Camphenephosphonic acid; 6-Chloro-8-(diethyl phosphonomethyl)-1,3-benzodioxane; 2-Thienylmethanephosphonic acid; Cyclohexanephosphonic acid; Ph$_2$(4-ClC$_6$H$_4$)CPO(OH)$_2$; Ph$_2$(4-BrC$_6$H$_4$)CPO(OH)$_2$; Ph$_2$(4-MeOC$_6$H$_4$)CPO(OH)$_2$; Ph$_2$(3-HOC$_6$H$_4$)CPO(OH)$_2$; Ph$_2$(4-MeC$_6$H$_4$)CPO(OH)$_2$; Ph$_2$(3-HOC$_6$H$_4$)CPO(OH)$_2$; Ph$_2$(4-MeC$_6$H$_4$)CPO(OH)$_2$; Ph$_2$(1-C$_{10}$H$_7$)CPO(OH)$_2$; Ph$_2$(2-C$_{10}$H$_7$)CPO(OH)$_2$; Ph$_2$(4-PhC$_6$H$_4$)CPO(OH)$_2$; Ph(4-PhC$_6$H$_4$)$_2$CPO(OH)$_2$; (4-PhC$_6$H$_4$)$_3$CPO(OH)$_2$; PhC(PO$_3$H$_2$):CH$_2$; PhCH:CHPO(OH)$_2$; PhMeC:CHPO(OH)$_2$; 3-ClC$_6$H$_4$CH:CHPO(OH)$_2$; 2-ClC$_6$H$_4$C CPO(OH)$_2$; 2,4-Me$_2$-C$_6$H$_2$CH:CHPO(OH)$_2$; 2,4,6-Me$_3$C$_6$H$_2$CH:CHPO(OH)$_2$; 4-EtC$_6$H$_4$CH:CHPO(OH)$_2$; 2-tert-BuC$_6$H$_4$CH:CHPO(OH)$_2$; 4-tert-BuC$_6$H$_4$CH:CHPO(OH)$_2$; 2-PhC$_6$H$_4$CH:CHPO(OH)$_2$; 4-PhC$_6$H$_4$CH:CHPO(OH)$_2$; 2-C$_{10}$H$_7$CH:CHPO(OH)$_2$; Ph$_2$C:CHPO(OH)$_2$; Ph$_2$CHCH$_2$PO(OH($_2$; (2-FC$_5$H$_4$)PhC:CHPO(OH)$_2$; (4-ClC$_6$H$_4$)PhC:CHPO(OH)$_2$; (4-ClC$_6$H$_4$)$_2$C:CHPO(OH)$_2$; (4-MeOC$_6$H$_4$)PhC:CHPO(OH)$_2$; (4-MeOC$_6$H$_4$)PhCHCH$_2$PO(OH)$_2$; (4-ClC$_6$H$_4$)(4-MeOC$_6$H$_4$)C:CHPO(OH)$_2$; (2-MeC$_6$H$_4$)PhC:CHPO(OH)$_2$; (2-MeC$_6$H$_4$)PhCHCH$_2$PO(OH)$_2$; (4-PhC$_6$H$_4$)PhC:CHPO(OH)$_2$; (4-PhC$_6$H$_4$)PhCHCH$_2$PO(OH)$_2$; (4-PhC$_6$H$_4$)(4-MeC$_6$H$_4$)C:CHPO(OH)$_2$; (1-C$_{10}$H$_7$)PhC:CHPO(OH)$_2$; (2-C$_{10}$H$_7$)PhC:CHPO(OH)$_2$; 2-(2-Fluorenyl)ethenephosphonic acid; 9,9-Diphenyl-9,10-dihydroanthracyl-10-methylenephosphonic acid; PhCH$_2$CH$_2$CH(PO$_3$H$_2$)Ph; PhCH$_2$CH$_2$CH$_2$CH$_2$PO(OH)$_2$; FCH$_2$PO(OCHMeEt)$_2$; ICH$_2$PO(OEt)$_2$; Cl$_3$CPO(OMe)$_2$; Cl$_3$CPO(OEt)$_2$; Cl$_3$CPO(OCH$_2$CH:CH$_2$)$_2$; Cl$_3$CPO(OPr)$_2$; Cl$_3$CPO(OPr-iso)$_2$; Cl$_3$CPO(OBu)$_2$; Cl$_3$CPO(OBu-iso)$_2$; FCH$_2$CH$_2$PO(OEt)$_2$; ClCH$_2$CH$_2$PO(OH)$_2$; BrCH$_2$CH$_2$PO(OH)$_2$; BrCH$_2$ CHBr PO(OEt)$_2$; Br(CH$_2$)$_3$PO(OH)$_2$; NC(CH$_2$)$_3$PO(OEt)$_2$; Me$_2$CCl CH$_2$PO(OH)$_2$; n-C$_5$H$_{11}$CCl:CH PO(OH)$_2$; iso-Pr CH$_2$ CHCl PO(OH)$_2$; PhMeCCl PO(OH)$_2$; ClCH$_2$CClPh PO(OH)$_2$; BrCH$_2$CBrPh PO(OH)$_2$; BrCH:CPh PO(OH)$_2$; (2-ClC$_6$H$_4$)CCl:CH PO(OH)$_2$; (2-MeOC$_6$H$_4$)CCl:CH PO(OH)$_2$; (4-MeOC$_6$H$_4$)CCl:CH PO(OH)$_2$; PhCH$_2$CCl:CH PO(OH)$_2$; Chlorofenchenephosphonic acid; H$_2$HCH$_2$PO(OH)$_2$; n-C$_{17}$H$_{35}$CO NHCH$_2$PO(OH)$_2$; PhCO NHCH$_2$PO(OH)$_2$; MeNHCH$_2$PO(OH)$_2$; n-C$_{17}$H$_{35}$CO NMe CH$_2$PO(OH)$_2$; H$_2$NCH$_2$CH$_2$PO(OH)$_2$; Et$_2$NCH$_2$CH$_2$PO(OEt)$_2$; Bu$_2$NCH$_2$CH$_2$PO(OEt)$_2$; Ph$_2$N C(PO$_3$H$_2$)(Me)Cl; H$_2$NCH$_2$CH$_2$CH$_2$PO(OH)$_2$; PhNH CH$_2$CH$_2$CH$_2$PO(OH)$_2$; H$_2$N(CH$_2$)$_4$PO(OH)$_2$; H$_2$N(CH$_2$)$_5$PO(OH)$_2$; H$_2$N(CH$_2$)$_{10}$-PO(OH)$_2$; PhCH(NH$_2$)PO(OH)$_2$; PhMeC(NH$_2$)PO(OH)$_2$; HOCH$_2$PO(OH)$_2$; PhCH$_2$OCH$_2$PO(OEt)$_2$; PhCH$_2$OCH$_2$PO(OBu)$_2$; HOCH$_2$CH$_2$PO(OH)$_2$; PhOCH$_2$CH$_2$PO(OH)$_2$; MeCHOH PO(OH)$_2$; Me$_2$C(OH)PO(OH)$_2$; Me(ClCH$_2$)C(OH)PO(OH)$_2$; EtCHOH PO(OH)$_2$; MeEtC(OH) PO(OH)$_2$; iso-PrCHOH PO(OH)$_2$; PrMeC(OH) PO(OH)$_2$; iso-BuCHOH PO(OH)$_2$; Et$_2$C(OH) PO(OH)$_2$; (Me$_3$C)MeC(OH) PO(OH)$_2$; EtPrC(OH) PO(OH)$_2$; n-C$_6$H$_{13}$CHOH PO(OH)$_2$; PhCH(OH) PO(OH)$_2$; PhMeC(OH) PO(OH)$_2$; Ph$_2$C(OH) PO(OH)$_2$; (PhCH$_2$CH$_2$)$_2$C(OH) PO(OH)$_2$; (PhCH$_2$)$_2$C(OH) PO(OH)$_2$; (PhCH$_2$CH$_2$)PhC(OH) PO(OH)$_2$; HOCH$_2$ C(OH)Ph PO(OH)$_2$; MeCOCH$_2$CH$_2$PO(OH)$_2$; PhCO CCl$_2$ PO(OH)$_2$; MeCOCH$_2$CMe$_2$ PO(OH)$_2$; (PhCOCH$_2$)PhCH PO(OH)$_2$; (PhCO CHBr)PhCH PO(OH)$_2$; (4-MeOC$_6$H$_4$) (PhCOCH$_2$)CH PO(OH)$_2$); (4-ClC$_6$H$_4$COCH$_2$)PhCH PO(OH)$_2$; (4-ClC$_6$H$_4$COCHBr)PhCH PO(OH)$_2$; (PhCO) (PhCOCH$_2$) CH PO(OH)$_2$; (PhCH:CH CO CH$_2$)PhCH PO(OH)$_2$; (PhCHBr CHBr CO CH$_2$)PhCH PO(OH)$_2$; (PhCH:CBr CO CH$_2$)PhCH PO(OH)$_2$; (Ph CO CH$_2$) (PhCH:CH)CH PO(OH)$_2$; 9-Keto-10-hydroxyphenanthrene-10-phosphonic acid; 3-Phosphonomethylene camphor; HO$_2$C PO(OH)$_2$; HO$_2$CCH$_2$PO(OH)$_2$; HO$_2$C CHMe PO(OH)$_2$; HO$_2$CCMeOH PO(OH)$_2$; HO$_2$C CH$_2$CH$_2$PO(OH)$_2$; HO$_2$C CHEt PO(OH)$_2$; HO$_2$C CH$_2$ CH$_2$ CH$_2$PO(OH)$_2$; HO$_2$C CMe$_2$ PO(OH)$_2$; n-C$_6$H$_{13}$CH(CO$_2$H)PO(OH)$_2$; HO$_2$C(CH$_2$)$_{10}$ PO(OH)$_2$; HO$_2$C CH(CH$_2$Ph) PO(OH)$_2$; (HO$_2$C CO CH$_2$)PhCH PO(OH)$_2$; (HO$_2$C)$_2$CH PO(OH)$_2$; (HO)$_2$P(O)CH$_2$PO(OH)$_2$; (HO)$_2$P(O)CH$_2$CH$_2$PO(OH)$_2$; (HO$_2$P(O)(CH$_2$)$_3$PO(OH)$_2$; (HO)$_2$P(O)CH$_2$OCH$_2$PO(OH)$_2$; p-(HO)$_2$P(O)CH$_2$ C$_6$H$_4$CH$_2$PO(OH)$_2$; 2,4-Me$_2$C$_6$H$_3$(1,5)(CH$_2$PO$_3$H$_2$)$_2$; 2,5-Me$_2$C$_6$H$_3$(1,4)(CH$_2$PO$_3$H$_2$)$_2$; 1,4-(HO)$_2$P(O)CH:CPh C$_6$H$_4$ CPh:CHPO(OH)$_2$; 1,3,5-Me$_3$C$_6$H(2,4)(CH$_2$PO$_3$H$_2$)$_2$; 9,9,10-Di-(phosphonomethyl)-anthracene; PhPO(OH)$_2$; 3-O$_2$NC$_6$H$_4$PO(OH)$_2$; 3-H$_2$NC$_6$H$_4$PO(OH)$_2$; 3-EtO$_2$CNH C$_6$H$_4$PO(OH)$_2$; 3-H$_2$N-2,4,6-Br$_3$C$_6$H PO(OH)$_2$; 4-H$_2$NC$_6$H$_4$PO(OH)$_2$; 4-H$_2$N-3-O$_2$N C$_6$H$_3$PO(OH)$_2$; 3-ClC$_6$H$_4$PO(OH)$_2$; 3-BrC$_6$H$_4$PO(OH)$_2$; 3-IC$_6$H$_4$PO(OH)$_2$; 4-ClC$_6$H$_4$PO(OH)$_2$; 4-Cl-3-O$_2$NC$_6$H$_3$PO(OH)$_2$; 4-Cl-3-H$_2$NC$_6$H$_3$PO(OH)$_2$; 4-(HO$_2$CCH$_2$NH)-3-O$_2$NC$_6$H$_3$PO(OH)$_2$O; 4-PhO-3-O$_2$NC$_6$H$_3$PO(OH)$_2$; 4-(2-ClC$_6$H$_4$O)-3-O$_2$NC$_6$H$_3$PO(OH)$_2$; 4-(4-ClC$_6$H$_4$O)-3-O$_2$NC$_6$H$_3$PO(OH)$_2$; 4-HO-3-O$_2$NC$_6$H$_3$PO(OH)$_2$; 4-

Me$_2$NC$_6$H$_4$PO(OH)$_2$; 2,5-Cl$_2$C$_6$H$_3$PO(OH)$_2$; 4-BrC$_6$H$_4$PO(OH)$_2$; 4-Br-3-O$_2$NC$_6$H$_3$PO(OH)$_2$; 4-IC$_5$H$_4$PO(OH)$_2$; 4-MeOC$_6$H$_4$PO(OH)$_2$; 4-EtOC$_6$H$_4$PO(OH)$_2$; 4-PhOC$_6$H$_4$PO(OH)$_2$; 4-BrC$_6$H$_4$OC$_6$H$_4$PO(OH)$_2$; 2-MeC$_6$H$_4$PO(OH)$_2$; 2-Me-5-ClC$_6$H$_3$PO(OH)$_2$; 2-HO$_2$CC$_6$H$_4$PO(OH)$_2$; 3-MeC$_6$H$_4$PO(OH)$_2$; 3-Me-6-ClC$_6$H$_3$PO(OH)$_2$; 3-Me-2,5,6-Cl$_3$C$_6$H PO(OH)$_2$; 3-Me-6-BrC$_6$H$_3$PO(OH)$_2$; 3-HO$_2$CC$_6$H$_4$PO(OH)$_2$; 4-MeC$_6$H$_4$PO(OH)$_2$; 4-Me-3-O$_2$NC$_6$H$_3$PO(OH)$_2$; 4-Me-3-H$_2$NC$_6$H$_3$PO(OH)$_2$; 4-Me-3-ClC$_6$H$_3$PO(OH)$_2$; 4-HO$_2$CC$_6$H$_4$PO(OH)$_2$; 4-HO$_2$C-3-Cl-C$_6$H$_3$PO(OH)$_2$; 4-EtC$_6$H$_4$PO(OH)$_2$; 2,4-Me$_2$C$_6$H$_3$PO(OH)$_2$;3,5-Me$_2$C$_6$H$_3$PO(OH)$_2$; 2,5-Me$_2$C$_6$H$_3$PO(OH)$_2$; 2,4,5-Me$_3$C$_6$H$_2$PO(OH)$_2$; 2,4,5-Me$_3$6-ClC$_6$HPO(OH)$_2$; 2,4-Me$_2$-5-(HO$_2$C)C$_6$H$_2$PO(OH)$_2$; 4-Me-2,5-(HO$_2$C)$_2$C$_6$H$_2$ PO(OH)$_2$; 2,4,6-Me$_3$C$_6$H$_2$PO(OH)$_2$; 2 (or 5)-Me-5(or 2)-iso-PrC$_6$H$_3$PO(OH)$_2$; 1-C$_{10}$H$_7$PO(OH)$_2$; PhC$_6$H$_4$PO(OH)$_2$; 4-PhCH$_2$CH$_2$C$_6$H$_4$PO(OH)$_2$; 2-Thiophenephosphonic acid; 9-Acridine phosphonic acid; 1-Phenyl-5-chloro-3-methyl-1-pyrazolphosphonic acid; Me$_2$PO(OH); Et$_2$PO(OH); Pr$_2$PO(OH); Bu$_2$PO(OH); iso-Bu$_2$PO(OH); iso-Am$_2$PO(OH); MeEtPO(OH); (PhCH$_2$)$_2$PO(OH); (4-O$_2$NC$_6$H$_4$CH$_2$)$_2$-PO(OH); (HOCH$_2$)$_2$PO(OH); (Me$_2$C(OH))$_2$ PO(OH); (Ph CHOH)$_2$ PO(OH); (2-HOC$_6$H$_4$ CHOH)$_2$ PO(OH); (4-iso-PrC$_6$H$_4$ CHOH)$_2$PO(OH); (HOCH$_2$) (PhCHOH)PO(OH); (MeCHOH)(PhMeCOH)PO(OH); (Me$_2$COH)(PhCHOH)PO(OH); (MeEtCOH)(PhCHOH)PO(OH); (MePrCOH)(PhCHOH)PO(OH); (Et$_2$COH)(PhCHOH)PO(OH); (iso-BuCHOH)(PhCHOH)PO(OH); (iso-BuCHOH)$_2$PO(OH); (n-C$_6$H$_{13}$CHOH)$_2$PO(OH); (Me$_2$COH)(MeCHOH)PO(OH); (Me$_2$COH)(n-C$_6$H$_{13}$CHOH)PO(OH); (MeEtCOH)(n-C$_6$H$_{13}$CHOH)PO(OH); (Me CO CH$_2$ CMe$_2$)BuPO(OH); (PhCO CH$_2$ CHPh)BuPO(OH); PhMePO(OH); PhEtPO(OH); Ph(iso-Pr)PO(OH); Ph(iso-Bu)PO(OH); Ph(Ph$_3$C) PO(OH); Ph(Cl$_3$C)PO(OH); Ph(HO$_2$C CH$_2$)PO(OH); Ph(HO$_2$C CHMe)PO(OH); Ph(MeCHOH)PO(OH); Ph(Me CO CH$_2$ CMe$_2$)PO(OH); Ph(Ph CO CH$_2$ CHPh) PO(OH); Ph(Ph CO CHBr CHPh)PO(OH); Ph(PhCH:CH CO CH$_2$CHPh)PO(OH); Ph(Ph CHBr CHBr CO CH$_2$ CHPh)PO(OH); Ph(Ph CH:CBr CO CH$_2$ CHPh)PO(OH); Ph(Ph CHOH) PO(OH); (4-BrC$_6$H$_4$)PhPO(OH); Me(4-MeC$_6$H$_4$)PO(OH); (Me CO CH$_2$ CMe$_2$)(4-MeC$_6$H$_4$)PO(OH); Ph(4-MeC$_6$H$_4$)PO(OH); (PhCH$_2$)(4-MeC$_6$H$_4$) PO(OH); Ph(2,4,5-Me$_3$C$_6$H$_2$)PO(OH); Ph$_2$PO(OH); (2-ClC$_6$H$_4$)$_2$PO(OH); (4-ClC$_6$H$_4$)$_2$PO(OH); (4-ClC$_6$H$_4$)(4-H$_2$NC$_6$H$_4$)PO(OH); (4-H$_2$NC$_6$H$_4$)$_2$PO(OH); (2-MeOC$_6$H$_4$)$_2$PO(OH); (4-MeOC$_6$H$_4$)$_2$PO(OH); (4-Et$_2$NC$_6$H$_4$)$_1$PO(OH); (2-MeC$_6$H$_4$)$_2$PO(OH); (4-MeC$_6$H$_4$)$_2$PO(OH); (4-MeC$_6$H$_4$(4-HO$_2$CC$_6$H$_4$)PO(OH); (2,4,5-Me$_3$C$_6$H$_2$)$_2$PO(OH); (1-C$_{10}$H$_7$)$_2$PO(OH); Dicamphorylphosphonic acid; Di-2-pyrrylphosphonic acid; Di-3-indolylphosphonic acid; Di-2-methyl-3-indolylphosphonic acid; 5,10-Dihydro-10-phenophosphazinic acid, and the like.

Other compounds which contain both phosphorous and halogen may also be used in the process of this invention such as, e.g., EtPCl$_4$; PrPCl$_4$; iso-PrPCl$_4$; iso-BuPCl$_4$; iso-AmPCl$_4$; Me$_2$C:CH CHCl CH$_2$PCl$_4$; PhPBr$_2$Cl$_2$; PhPBr$_4$; 4-ClC$_6$H$_4$PCl$_4$; 4-ClC$_6$H$_4$PCl$_2$Br$_2$; 4-BrC$_6$H$_4$PCl$_4$; 4-MeOC$_6$H$_4$PCl$_4$; 4-EtOC$_6$H$_4$PCl$_4$; 4-PhOC$_6$H$_4$PCl$_4$; 4-Me$_2$NC$_6$H$_4$PCl$_4$; 4-Me$_2$NC$_6$H$_4$PCl$_2$Br$_2$; 2-MeC$_6$H$_4$PCl$_4$; 3-MeC$_6$H$_4$PCl$_4$; 4-MeC$_6$H$_4$PCl$_4$; 2-Cl-4-MeC$_6$H$_3$PCl$_4$; 4-MeC$_6$H$_4$PCl$_2$Br$_2$; 4-MeC$_6$H$_4$PBr$_4$; 2,5-Me$_2$C$_6$H$_3$PCl$_4$; 4-EtC$_6$H$_4$PCl$_4$; 2,4,5-Me$_3$C$_6$H$_2$PCl$_4$; 2,4,6-Me$_3$C$_6$H$_2$PCl$_4$; 2(or 5)-Me-5(or 2)-iso-Pr-C$_6$H$_3$PCl$_4$; 4-PhCH$_2$C$_6$H$_4$PCl$_4$; 1-C$_{10}$H$_7$PCl$_4$; 1-C$_{10}$H$_7$PCl$_2$Br$_2$; PhC$_6$H$_4$PCl$_4$; 2-Indenylphosphorus tetrachloride; 2-Thienylphosphorus tetrachloride; Ph$_2$PCl$_3$; (4-BrC$_6$H$_4$)PhPCl$_3$; (4-MeC$_6$H$_4$)PhPCl$_3$; (4-MeC$_6$H$_4$)$_2$PCl$_3$; 2,4,5-Me$_3$C$_6$H$_2$PhPCl$_3$; Et$_3$PCl$_2$; Et$_2$PhPCl$_2$; Ph$_2$(PhCH$_2$)PCl$_2$; Ph$_2$(PhCH$_2$)PClBr; Ph$_3$PCl$_2$; Ph$_3$PBr$_2$; (4-MeC$_6$H$_4$)$_3$PCl$_2$; (2,4,5-Me$_3$C$_6$H$_2$)$_3$PCl$_2$; (1-C$_{10}$H$_7$)$_3$PCl$_2$; (1-C$_{10}$H$_7$)$_3$PBr$_2$; MePOCl$_2$; EtPOCl$_2$; ClCH$_2$CH$_2$POCl$_2$; BrCH$_2$CH$_2$POCl$_2$; PrPOCl$_2$; iso-PrPOCl$_2$; Me(CH$_2$:)CPOCl$_2$; iso-BuPOCl$_2$; iso-AmPOCl$_2$; iso-Bu CHCl POCl$_2$; Cyclohexanephosphonyl dichloride; Me$_2$POCl; MeEtPOCl; Et$_2$POCl; Pr$_2$POCl; Bu$_2$POCl;

MeC:CH CMe$_2$ POClO;

PhPOCl$_2$; 4-ClC$_6$H$_4$POCl$_2$; 4-BrC$_6$H$_4$POCl$_2$; 4-MeOC$_6$H$_4$POCl$_2$; 4-EtOC$_6$H$_4$POCl$_2$; 2-MeC$_6$H$_4$POCl$_2$; 3-MeC$_6$H$_4$POCl$_2$; 4-MeC$_6$H$_4$POCl$_2$; 2-Cl-4-MeC$_6$H$_3$POCl$_2$; 4-MeC$_6$H$_4$POBrCl; 4-MeC$_6$H$_4$POBr$_2$; 1,2-Me$_2$C$_6$H$_3$POCl$_2$; 2,5-Me$_2$C$_6$H$_3$POCl$_2$; 4-EtC$_6$H$_4$POCl$_2$; 2,4,5-Me$_3$C$_6$H$_2$POCl$_2$; 2,4,6-Me$_3$C$_6$H$_2$POCl$_2$; 4-(PhCCl$_2$)C$_6$H$_4$POCl$_2$; 4-(PhCH$_2$CH$_2$)C$_6$H$_4$POCl$_2$; (PhCh$_2$)$_2$CHPOCl$_2$; PhC$_6$H$_4$POCl$_2$; 1-C$_{10}$H$_7$POCl$_2$; 2-Thiophenephosphonyl dichloride; MePhPOCl; EtPhPOCl; Ph$_2$POCl; (2-ClC$_6$H$_4$)$_2$POCl; (4-ClC$_6$H$_4$)$_2$POCl; (4-O$_2$NC$_6$H$_4$)$_2$POCl; (4-MeC$_6$H$_4$)PhPOCl; (2,4,5-Me$_3$C$_6$H$_2$)PhPOCl; (2-MeC$_6$H$_4$)$_2$POCl; (4-MeC$_6$H$_4$)$_2$POCl; (1-C$_{10}$H$_7$)$_2$ POCl; Ph$_3$CPOCl$_2$; Ph$_3$CPO(OH)Cl; (4-ClC$_6$H$_4$)Ph$_2$CPO Cl$_2$; (4-BrC$_6$H$_4$)Ph$_2$CPOCl$_2$; (4-MeOC$_6$H$_4$)Ph$_2$CPOCl$_2$; (3-MeOC$_6$H$_4$)Ph$_2$CPOCl$_2$; (4-O$_2$NC$_6$H$_4$)Ph$_2$CPOCl$_2$; (4-MeC$_6$H$_4$)Ph$_2$CPOCl$_2$; (1-C$_{10}$H$_7$)Ph$_2$CPOCl$_2$; (2-C$_{10}$H$_7$)Ph$_2$CPOCl$_2$; (4-PhC$_6$H$_4$)Ph$_2$CPOCl$_2$; (4-PhC$_6$H$_4$)$_2$PhCPOCl$_2$; (4-PhC$_6$H$_4$)$_3$CPOCl$_2$; EtPSCl$_2$; PrPSCl$_2$; iso-BuPSCl$_2$; iso-AmPSCl$_2$; MeEtPSCl; Et$_2$PSCl; Pr$_2$PSCl; Bu$_2$PSCl; PhPSCl$_2$; 4-MeC$_6$H$_4$PSCl$_2$; MePhPSCl; EtPhPSCl; Ph$_2$PSCl; (2-ClC$_6$H$_4$)$_2$PSCl; (4-ClC$_6$H$_4$)$_2$PSCl; (4-O$_2$NC$_6$H$_4$)$_2$PSCl; (4-Me$_2$NC$_6$H$_4$)$_2$PSCl; (2-MeC$_6$H$_4$)$_2$PSCl; (4-MeC$_6$H$_4$)$_2$PSCl; (4-MeC$_6$H$_4$)PhPSCl; (1-C$_{10}$H$_7$)$_2$PSCl; and the like.

Phosphonous acids also may be used in the process of this invention. Thus, one may utilize MePO$_2$H$_2$; EtPO$_2$H$_2$; PrPO$_2$H$_2$; CH$_2$:CH CH$_2$PO$_2$H$_2$; iso-PrPO$_2$H$_2$; iso-PrPO$_2$H$_2$; iso-BuPO$_2$H$_2$; iso-AmPO$_2$H$_2$; n-C$_7$H$_{15}$PO$_2$H$_2$; n-C$_8$H$_{17}$PO$_2$H$_2$; PhCH$_2$PO$_2$H$_2$; Ph$_3$CPO$_2$H$_2$; (4-Me$_2$NC$_6$H$_4$)$_2$CHPO$_2$H$_2$; Me CHOH PO$_2$H$_2$; Me$_2$COH PO$_2$H$_2$; MeEtCOH PO$_2$H$_2$; MePrCOH PO$_2$H$_2$; Et$_2$COH PO$_2$H$_2$; iso-Bu CHOH PO$_2$H$_2$; n-C$_6$H$_{13}$ CHOH PO$_2$H$_2$; Ph CHOH PO$_2$H$_2$; Ph$_2$COH PO$_2$H$_2$; MePhCOH PO$_2$H$_2$; (2-HOC$_6$H$_4$) CHOH PO$_2$H$_2$; (4-iso-PrC$_6$H$_4$) CHOH PO$_2$H$_2$; Me CO CH$_2$PO$_2$H$_2$; (1,3-)C$_6$H$_4$(CHOH PO$_2$H$_2$)$_2$; PhPO$_2$H$_2$; 4-ClC$_6$H$_4$PO$_2$H$_2$; 4-BrC$_6$H$_4$PO$_2$H$_2$; 4-MeOC$_6$H$_4$PO$_2$H$_2$; 4-EtOC$_6$H$_4$PO$_2$H$_2$; 2-O$_2$NC$_6$H$_4$PO$_2$H$_2$; 4-O$_2$NC$_6$H$_4$PO$_2$H$_2$; 4-H$_2$NC$_6$H$_4$PO$_2$H$_2$; 4-Me$_2$NC$_6$H$_4$PO$_2$H$_2$; 4-(PhCH$_2$)MeNC$_6$H$_4$PO$_2$H$_2$; 4-PhMeNC$_6$H$_4$PO$_2$H$_2$; 4-Et$_2$NC$_6$H$_4$PO$_2$H$_2$; 4(Me$_2$N)-2-MeC$_6$H$_3$PO$_2$H$_2$; 4-(Et$_2$N)-2-MeC$_6$H$_3$PO$_2$H$_2$; 3-MeC$_6$H$_4$PO$_2$H$_2$; 2-MeC$_6$H$_4$PO$_2$H$_2$; 4-MeC$_6$H$_4$PO$_2$H$_2$; 4-Me-3-ClC$_6$H$_3$PO$_2$H$_2$; 4-EtC$_6$H$_4$PO$_2$H$_2$; 2,4-Me$_2$C$_6$H$_3$PO$_2$H$_2$; 2,5-Me$_2$C$_6$H$_3$PO$_2$H$_2$; 2,4,5-Me$_3$C$_6$H$_2$PO$_2$H$_2$; 2,4,6-Me$_3$C$_6$H$_2$PO$_2$H$_2$; 2(or 5)-Me-5(or 2)-iso-PrC$_6$H$_3$PO$_2$H$_2$;

1-C$_{10}$H$_7$PO$_2$H$_2$; 2-C$_{10}$H$_7$PO$_2$H$_2$; 4-PhC$_6$H$_4$PO$_2$H$_2$; 4-PhCH$_2$C$_6$H$_4$PO$_2$H$_2$; 4-PhCH$_2$CH$_2$C$_6$H$_4$PO$_2$H$_2$; 1,2,7,8-Dibenzoxanthene-9-phosphonous acid; 2-Thiophenephosphonous acid; 4,4'-Biphenyldiphosphonous acid, and the like.

Phosphites and thiophosphites may also be used in the process of this invention. Some suitable phosphites and thiophosphites include, for example, (BuO)$_3$P; (iso-BuO)$_3$P; (iso-AmO)$_3$P; (2-C$_8$H$_{17}$O)$_3$P; PhOP(OCH$_2$CH$_2$Cl)$_2$; (PhO)$_2$POCH$_2$CH$_2$Cl; (PhO)$_2$(PrO)P; (PhO)$_2$(BuO)P; (PhO)$_3$P; (PhO)$_2$(2-ClC$_6$H$_4$O)P; (4-ClC$_6$H$_4$O)$_3$P; (2-MeOC$_6$H$_4$O)$_3$P; (4-O$_2$NC$_6$H$_4$O)$_3$P; (p-tert-BuC$_6$H$_4$O)(PhO)$_2$P; (p-tert-BuC$_6$H$_4$O)(PhO)$_2$P; (2-Me-5-iso-Pr-C$_6$H$_3$O)(2-ClC$_6$H$_4$O)$_2$P; (2-MeC$_6$H$_4$O)$_3$P; (3-MeC$_6$H$_4$O)$_3$P; (4-MeC$_6$H$_4$O)$_3$P; Tripseudocumyl phosphite; (4-tert-BuC$_6$H$_4$O)$_3$P; (4-Me$_3$CCH$_2$CMe$_2$C$_6$H$_4$O)$_3$P; (2-PhC$_6$H$_4$O)(PhO)$_2$P; (2-PhC$_6$H$_4$O)$_2$(PhO)P; (2-PhC$_6$H$_4$O)$_3$P; Tri-o-cyclohexylphenyl phosphite; (1-C$_{10}$H$_7$O)$_3$P; (2-C$_{10}$H$_7$O)$_3$P; Tri-1-(2,4-dibromo)naphthyl phosphite; Tri-2-(1,6-dibromo)naphthyl phosphite; Tri-2-decahydronaphthyl phosphite; Tri-1-anthryl phosphite; Tri-1-menthyl phosphite;

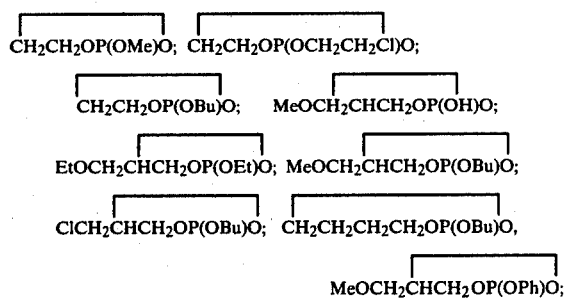

o-C$_6$H$_4$O$_2$POCH$_2$CH$_2$Cl; o-C$_6$H$_4$O$_2$POBu; o-C$_6$H$_4$O$_2$POBu-iso; o-C$_6$H$_4$O$_2$POPh; o-C$_6$H$_4$O$_2$POC$_6$H$_4$Me-o; o-C$_6$H$_4$O$_2$POC$_6$H$_4$OH-o; o-C$_6$H$_4$O$_2$POC$_6$H$_4$Me-o; o-C$_6$H$_4$O$_2$POC$_6$H$_4$Me-m; o-C$_6$H$_4$O$_2$POC$_6$H$_4$Me-p; Tri-o-phenylene diphosphite; (EtO)$_2$(EtS)P; (EtO)(EtS)$_2$P; (EtS)$_3$P; (Pro)$_2$(PrS)P; (PrO)(EtS)$_2$P; (PrS)$_3$P; (BuS)$_3$P; (PhS)$_3$P.

One may also use the phosphorus compounds of the formula

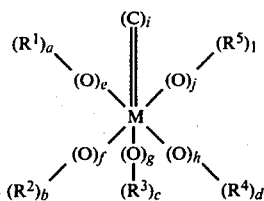

wherein M is selected from the group consisting of phosphorus, antimony, and arsenic; wherein C is selected from the group consisting of oxygen and sulfur; wherein a, b, c, d, e, f, g, h, i, j, and l are integers independently selected from the group consisting of 0 and 1 and a+b+c+d+l+i is from 1-5; and wherein R$^1$, R$^2$, R$^3$, R$^4$, and R$^5$ are independently selected from the group consisting of hydrogen, hydroxyl, fluorine, chlorine, bromine, iodine, alkyl containing from about 1 to about 12 carbon atoms, haloalkyl containing from about 1 to about 12 carbon atoms, (X)$_m$R$^6$C wherein X is selected from the group consisting of hydrogen, fluorine, chlorine, bromine, iodine, and mixtures thereof, m is an integer of from about 1 to about 3, and R$^6$ is alkylene containing from about 1 to about 6 carbon atoms, and

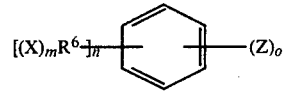

wherein n and o are integers independently selected from the group consisting of 0, 1, 2, 3, 4, and 5, and Z is selected from the group consisting of hydrogen, phenyl, nitro, fluorine, chlorine, bromine, and iodine. These compounds are well known to those skilled in the art and are described in, e.g., G. M. Kosolapoff's "Organophosphorus Compounds" which was published by John Wiley and Sons, Inc., in 1950. The Kosolapoff book is incorporated by reference in toto into this specification.

In the third and final stage reaction of the present process, the hexachlorinated product of the second stage reaction is reacted in the vapor phase with chlorine so as to yield the desired high purity hexachlorocyclopentadiene. In this stage cyclopentane and cyclopentenes now containing an average of six chlorine atoms are converted to hexachlorocyclopentadiene.

Since the reaction is performed in the vapor phase, it is necessary to vaporize the hexachlorinated reactant. This can be readily performed by heating to a temperature of at least 400° C., preferably 400°–700° C., in the presence of the requisite quantity of chlorine. The theoretical quantity of chlorine for this reaction is approximately 2 moles of chlorine per mole of chlorinated cyclic compound. It is desirable to have present an excess of chlorine to prevent undesirable polymerization. One may use a chlorinated cyclic compound/chlorine mole ratio of from about 1:2 to about 1:4.

The actual reaction temperature should be above about 450° C., with the optimum temperature depending in part upon the reaction time. Temperatures above about 500° C. are preferred with excessively high temperatures not being of value. Accordingly reaction temperatures between about 500° C. to 700° C. are of practical value.

At the above temperatures, the reaction time is extremely short, in the order of a few seconds. Generally, reaction times of from about 0.5 to 5 seconds are sufficient, with the precise time depending upon the reaction conditions and equipment.

As in the case of the liquid phase reactions, the vapor phase reaction is normally conducted on a continuous basis. Also, as in the case of the liquid reactions, no catalyst is required.

Thus, it can be seen that the present process utilizes three reactions or stages, two in the liquid phase and one in the vapor phase in producing substantially quantitative yields of good purity hexachlorocyclopentadiene, i.e. 90–98% assay. If even higher purity product is required, this can be readily accomplished by fractional distillation. By use of this method of purification hexachlorocylopentadiene of 98% and higher assay is obtainable.

The following examples are provided for the purpose of further illustration only and are not intended to be limitative of the invention. Unless otherwise specified, all parts are by weight, all weights are in grams, all temperatures are in degrees centigrade, and all volumes are in milliliters.

EXAMPLE 1

Carbon tetrachloride was placed in a 5-necked glass reaction flask. Chlorine gas was added so as to saturate the carbon tetrachloride. The purpose of the carbon tetrachloride was to insure the presence of the necessary excess of chlorine and required dilution of cyclopentadiene. Cyclopentadiene was then continuously added to the reaction mixture while the chlorine gas was continuously incorporated. Throughout the reaction, the mixture was maintained at a temperature of 40 degrees centigrade. The desired tetrachlorinated products were then freed from the carbon tetrachloride by distillation in the presence of excess chlorine. Additional chlorine was then injected, and the temperature was maintained at 150 degrees centigrade. Approximately quantitative yields of the desired hexachlorinated second stage product were recovered; analysis indicated that it contained 75.7 percent of chlorine.

EXAMPLE 2

Cyclopentadiene is cooled to a temperature of about −20 degrees Centigrade.

The cooled cyclopentadiene is continuously fed along with chlorine gas to a first-stage reactor. About 2 moles of chlorine per mole of cyclopentadiene are continuously fed to the first-stage reactor, and the reaction mixture is maintained at a temperature of about 45 degrees centigrade. The reaction is continued until a partially chlorinated product with a specific gravity of from about 1.50 to about 1.60 is obtained; this product is then fed to the second-stage reactor.

EXAMPLE 3

A partially chlorinated cyclopentadiene produced in substantial accordance with the procedure of Example 2 with a specific gravity of 1.540 was continually fed to a reactor together with gaseous chlorine and 75 parts per million of triphenyl phosphine (by weight of the partially chlorinated cyclopentadiene); the reaction mixture was maintained at a temperature of 169–173 degrees centigrade. The feed rates of the gaseous chlorine and the partially chlorinated cyclopentadiene were adjusted to a chlorine/cyclopentadiene mole ratio of about 5.87; about 30 mole percent of unreacted chlorine was present in the system. The reaction time was about 5.7 hours, and a chlorinated product with a specific gravity of about 1.665 was continuously removed from the reaction system. The reaction temperatures were held by the use of a controlled cooling wherein, once the reaction was initiated, no heating was required.

Once during this reaction the chlorine feed was inadvertently stopped for a period of about 4.0 hours; during this period, the temperature of the reaction mixture was maintained at 169–173 degrees centigrade. When the chlorine feed to the system was resumed, the reaction "started up" within a period of less than 60 minutes, within 60 minutes the reaction mixture became exothermic, and cooling was applied to the reaction mixture to keep the reaction temperature at from 169–173 degrees centigrade.

The product produced in this second-stage reaction was analyzed. It contained about 32.5 percent of a combination of tri-, tetra-, and octochlorinated components; and it contained about 67.5 percent of a combination of penta-, hexa-, and heptachlorinated components.

COMPARATIVE EXAMPLE 4

A partially chlorinated cyclopentadiene produced in substantial accordance with the procedure of Example 2 with a specific gravity of 1.54 was continuously fed to a reactor together with gaseous chlorine; no triphenyl phosphine was introduced into the system. The reaction mixture was maintained at a temperature of 165–180 degrees centigrade. The feed rates were adjusted to a chlorine/cyclopentadiene mole ratio of about 5.87; about 30 mole percent of unreacted chlorine was present in the system. The reaction time was about 5.7 hours, and a chlorinated cyclopentadiene product with a specific gravity of about 1.675 was continuously removed from the reaction system. Heat had to be supplied to the reaction mixture in order to maintain the reaction temperature.

Once during this reaction the chlorine feed was inadvertently stopped for a period of about 4.0 hours; during this period, the reaction mixture was heated and maintained at a temperature of from 165–180 degrees centigrade. The chlorine feed to the system was resumed, and an attempt was made to "start up" the reaction again. It required a period of nearly 24 hours before the reaction proceeded at a rate equivalent to the one obtained before the chlorine feed was disrupted; and even after this period of time heat had to be supplied from an external heater to maintain the reaction temperature. The resulting product composition contained about 70% of the tri-, tetra- and octachlorocyclic compounds, while there were only about 30% of the penta-, hexa-, and heptachloro-products.

EXAMPLES 5-6

In substantial accordance with the procedure of Example 3, chlorinated cyclopentadiene second-stage product was prepared; different additives and/or different concentrations of the triphenyl phosphine additive were utilized.

Portions of this first-stage product were converted to second-stage product (specific gravity about 1.7) by charging them to a 4-neck 250 milliliter flask fitted with a stirrer, a thermometer, and a chlorine inlet and outlet; 250 grams of chlorinated cyclopentadiene with a specific gravity of about 1.55 were used in each experiment.

In each of these Examples, the reaction mixture was heated with a thermowatch-controlled heating mantle; heat was turned on, and chlorine was introduced into the flask at the rate of 0.08 pounds per hour until a reaction temperature of 168–172 degrees centigrade was reached. The chlorine flow rate was maintained at 0.2 pounds per hour until a product with a specific gravity of 1.70 (at 35° C.) was obtained.

Table 1 indicates the additive used and its concentration, the specific gravity of the chlorinated product produced, and the percentages of the tri-, tetra-, penta-, hexa-, hepta-, and octachlorinated components.

TABLE 1

| Example # | Additive/Concentration (ppm) | Sp. Gr. (@35° C.) | Composition of Product, % | | | | | |
|---|---|---|---|---|---|---|---|---|
| | | | $Cl_3$ | $Cl_4$ | $Cl_5$ | $Cl_6$ | $Cl_7$ | $Cl_8$ |
| 5 | triphenyl phosphine, 9.4 | 1.6995 | .43 | 4.91 | 6.3 | 37.4 | 42.7 | 7.7 |
| 6 | phosphoric acid, 85%, 1000 ppm | 1.701 | .96 | 6.2 | 6.9 | 40 | 39.2 | 6.4 |

EXAMPLE 7

The procedure described in Examples 5 and 6 was substantially repeated with the exception that no phosphorus compound was added during the chlorination. After seven hours of chlorination at a temperature of 168-172 degrees centigrade with excess chlorine at a rate of 0.2 pounds of chlorine per hour, a product with a density of 1.7048 was produced. Gas chromatographic analysis of this product indicated that it contained 35.8 percent (by weight) of pentachloro-, hexachloro- and heptachloro- products and 60.8 percent (by weight) of trichloro-, tetrachloro-, and octachloro- products.

EXAMPLE 8

The procedure of Example 7 was repeated with the exception that 31 parts per million of triphenyl phosphine were charged during the chlorination. The reaction product had a density of 1.6991 at 35 degrees centigrade. Gas chromatographic analysis of this product indicated that it contained 78.46 percent of pentachloro-, hexachloro-, and heptachloro- products and 21.13 percent (by weight) of trichloro-, tetrachloro-, and octachloro- products.

EXAMPLE 9

Chlorinated cyclic compound produced in substantial accordance with the procedure described in Example 3 was vaporized at a temperature of 300-340 degrees centigrade and fed into a vapor-phase reactor maintained at 550 degrees centigrade at a rate of 25 pounds per hour. Chlorine was continuously introduced to this reactor at a ratio of 6 moles of chlorine per mole of second-stage product. The average reaction time was about 1.2 seconds. Hexachlorocyclopentadiene recovered from the process was found by gas-liquid partition chromatographic analysis to be 95 percent hexachlorocyclopentadiene.

The above examples have been described for the purpose of illustration and not limitation. Many other modifications will suggest themselves to those skilled in the art; they are intended to be comprehended within the scope of this invention.

The embodiments of this invention in which an exclusive right or privilege are claimed are as follows:

1. A process for the production of hexachlorocyclopentadiene comprising the steps of:
   (a) reacting liquid cyclopentadiene and chlorine at a temperature of from about 0 to about 100 degrees centigrade until a minimum of four chlorine atoms has been added per mole of cyclopentadiene to form a first-stage product;
   (b) heating the resultant liquid reaction product of step (a) in a second stage at a temperature of from about 140 degrees centigrade to below about 200 degrees centigrade with chlorine in the presence of from about 0.0001 percent to about 1.0 percent (by weight) of a phosphorus compound until the reaction products of step (a) contain an average of about 6 chlorine atoms per molecule, based on cyclopentadiene starting material, wherein said phosphorus compound is

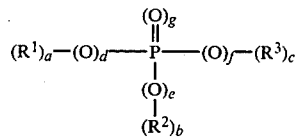

wherein a, b, c, d, e, f, and g are integers independently selected from the group consisting of 0 and 1, and $R^1$, $R^2$, and $R^3$, are independently selected from the group consisting of hydrogen, hydroxyl, fluorine, chlorine, bromine, iodine, alkyl containing from about 1 to 12 carbon atoms, phenyl, and halophenyl;
   (c) vaporizing and heating the resulting reaction products of step (b) in a third stage in the presence of chlorine to a temperature of above 450 degrees centigrade until at least a major portion of said products are converted to hexachlorocyclopentadiene; and
   (d) recovering therefrom hexachlorocyclopentadiene.

2. The process of claim 1, wherein g is 0.

3. The process of claim 2, wherein liquid cyclopentadiene and chlorine are reacted in a first-stage at a temperature of from about 20 to about 60 degrees centigrade until at least four chlorine atoms have been added per mole of cyclopentadiene.

4. The process of claim 3, wherein d, e, and f are 0.

5. The process of claim 4, wherein the resultant liquid reaction mixture is heated in a second stage at a temperature of from about 150 to about 185 degrees centigrade in the presence of from about 0.0005 to about 0.009 percent (by weight of said resultant liquid reaction mixture) of said phosphorus compound to produce a reaction product containing an average of 6 chlorine atoms per mole of cyclopentadiene.

6. The process of claim 5, wherein $R^1$, $R^2$, and $R^3$ are independently selected from the group consisting of alkyl containing from about 1 to about 12 carbon atoms, phenyl, and halophenyl.

7. The process of claim 6, wherein said phosphorus compound is triphenyl phosphine.

8. The process of claim 7, wherein from about 2 to 6 moles of chlorine per mole of tetrachlorinated material, in said resultant liquid reaction mixture, are heated in a second stage at a temperature of from about 150 to about 185 degrees centigrade.

9. The process of claim 8, wherein from about 0.0006 to about 0.0008 percent (by weight) of said triphenyl phosphine is heated with said resultant liquid reaction mixture and chlorine in the second stage.

10. The process of claim 1, wherein said phosphorus compound is phosphoric acid.

* * * * *